United States Patent [19]
Nishino et al.

[11] Patent Number: 5,962,456
[45] Date of Patent: Oct. 5, 1999

[54] N-ACYLPIPERAZINE DERIVATIVE, ANTI-ULCER DRUG, AND ANTIBACTERIAL DRUG

[75] Inventors: Chikao Nishino; Fumitaka Sato; Hirotada Fukunishi, all of Kanagawa, Japan

[73] Assignee: Shiseido Co., Ltd., Tokyo, Japan

[21] Appl. No.: 08/939,912

[22] Filed: Sep. 29, 1997

[30] Foreign Application Priority Data

Sep. 30, 1996 [JP] Japan ................................. 8-278872
Mar. 18, 1997 [JP] Japan ................................. 9-085937

[51] Int. Cl.$^6$ ................... A61K 31/495; C07D 401/04; C07D 401/12; C07D 295/192
[52] U.S. Cl. .................. 514/252; 544/365; 544/377; 544/388; 544/391; 544/360; 514/253; 514/255
[58] Field of Search ............................ 544/360, 365, 544/388, 391, 377; 514/252, 255, 253

[56] References Cited

U.S. PATENT DOCUMENTS

| | | | |
|---|---|---|---|
| 4,208,205 | 6/1980 | Fawzi | 504/337 |
| 5,756,505 | 5/1998 | Nishino et al. | 514/253 |

FOREIGN PATENT DOCUMENTS

| | | |
|---|---|---|
| 0 142 241 | 5/1985 | European Pat. Off. . |
| 0 416 410 A1 | 3/1991 | European Pat. Off. . |
| 0 497 740 A1 | 8/1992 | European Pat. Off. . |
| 0 611 232 A1 | 8/1994 | European Pat. Off. . |
| 0 735 031 A1 | 10/1996 | European Pat. Off. . |
| 964232 | 7/1964 | United Kingdom . |

OTHER PUBLICATIONS

Zlatoidsky, *Eur. J. Med. Chem. 31*, pp. 669–673 (1996).
LeDouarec et al, *Chemical Abstracts*, vol. 65, No. 2258c (1966).
Nishioka et al, *Chemical Abstracts*, vol. 125, No. 114686 (Aug. 26, 1996).

*Primary Examiner*—Emily Bernhardt
*Attorney, Agent, or Firm*—Snider & Chao LLP; Ronald R. Snider; Fei-Fei Chao, Ph.D.

[57] ABSTRACT

An N-acylpiperazine derivative or a salt thereof expressed by the following formula 1:

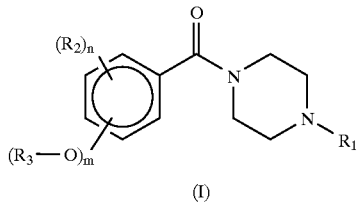

formula 1 wherein $R_1$ represents a pyridylcarbonyloxy lower alkyl group, a benzoylamino lower alkyl group, benzyl group, carbamoyl group, pyridyl group, or diphenylmethyl group;

$R_2$ represents a lower alkyl group or a lower alkoxy group;

n represents an integer of 0 to 2;

$R_3$ represents a hydrogen atom, an alkenyl group, or benzyl group; and m represents an integer of 1 to 3.

The N-acylpiperazine derivative or a salt thereof has an anti-ulcer effect, an antibacterial activity against *Helicobacter pyroli,* and high safety to be available for prevention or cure of various ulcers.

23 Claims, 4 Drawing Sheets

REACTION FORMULA A:

FIG.1

REACTION FORMULA B:

FIG.2

REACTION FORMULA C;

FIG.3

REACTION FORMULA D;

FIG.4

REACTION FORMULA E;

FIG.5

REACTION FORMULA F;

FIG.6

REACTION FORMULA G;

FIG.7

REACTION FORMULA H;

FIG.8

REACTION FORMULA I;

FIG.9

N-ACYLPIPERAZINE DERIVATIVE, ANTI-ULCER DRUG, AND ANTIBACTERIAL DRUG

RELATED APPLICATIONS

This application claims the priority of Japanese Patent Application No. 8-278872 filed on Sep. 30, 1996, and Japanese Patent Application No. 9-85937 filed on Mar. 18, 1997, which are incorporated herein by references.

FIELD OF THE INVENTION

The present invention relates to an N-acylpiperazine derivative and, in particular, to an N-acylpiperazine derivative having an antibacterial activity against *Helicobacter pyroli* or an anti-ulcer effect.

BACKGROUND OF THE INVENTION

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric acid secretion. Accordingly, it is important to suppress the acid secretion in order to prevent ulcer formation and to cure it.

On the other hand, it has been considered that *Helicobacter pyroli*, which is a rod normally existing in stomach, generates ammonia due to its strong urease activity, thereby inducing ulcer and persistence of itself. Since it persistently lives within mucus and mucosa, it becomes the greatest cause for recurrence of ulcer. Accordingly, it has been considered that the recurrence of ulcer can be prevented if this bacterium is sterilized.

Though various kinds of medicaments for curing ulcer have been conventionally developed, few medicaments have been known to have an effect for preventing stress ulcers from generating and an antibacterial activity against *Helicobacter pyroli*.

DISCLOSURE OF THE INVENTION

In view of the problems of the above-mentioned prior art, the object of the present invention is to provide a compound which is excellent in preventing ulcer from generating and to provide antibacterial drug against *Helicobacter pyroli* and anti-ulcer drug including such a compound as a main component.

As a result of the diligent studies conducted by the inventors, it has been found that a specific N-acylpiperazine derivative is effective against various kinds of ulcer due to its antibacterial property against *Helicobacter pyroli* or its acid secretion inhibition as a main action mechanism. Thus, the present invention has been accomplished.

Namely, an N-acylpiperazine derivative or a salt thereof in accordance with the present invention is expressed by the following formula 1:

formula 1

(I)

wherein
$R_1$ represents a pyridylcarbonyloxy lower alkyl group, a benzoylamino lower alkyl group, benzyl group, carbamoyl group, pyridyl group, or diphenylmethyl group;
$R_2$ represents a lower alkyl group or a lower alkoxy group;
n represents an integer of 0 to 2;
$R_3$ represents a hydrogen atom, an alkenyl group, or benzyl group; and
m represents an integer of 1 to 3.

An antibacterial drug against *Helicobacter pyroli* in accordance with the present invention comprises, as an effective ingredient, said N-acylpiperazine derivative or the pharmacologically acceptable salt thereof, together with a pharmaceutically acceptable carrier and/or adjuvant.

An anti-ulcer drug in accordance with the present invention comprises, as an effective ingredient, said N-acylpiperazine derivative or the pharmacologically acceptable salt thereof, together with a pharmaceutically acceptable carrier and/or adjuvant.

A method for the treatment of peptic ulcers in man or mammals in accordance with the present invention comprises administering an effective amount of said N-acylpiperazine derivative or the pharmacologically acceptable salt thereof to a host.

A method for the inhibition of acid secretion in stomach of man or mammals in accordance with the present invention comprises administering an effective amount of said N-acylpiperazine derivative or the pharmacologically acceptable salt thereof to a host.

A method for the inhibition of growth of *Helicobacter pyroli* in stomach of man or mammals in accordance with the present invention comprises administering an effective amount of said N-acylpiperazine derivative or the pharmacologically acceptable salt thereof to a host.

A method for the prevention of peptic ulcers in man or mammals in accordance with the present invention comprises administering an effective amount of said N-acylpiperazine derivative or the pharmacologically acceptable salt thereof to a host.

EXAMPLES

In the compound in accordance with the present invention, the "pyridylcarbonyloxy lower alkyl group" found at $R_1$ represents a group expressed by the following formula a:

formula a wherein p represents an integer of 1 to 4 and, preferably, 2.

The "benzoylamino lower alkyl group" found at $R_1$ represents a group expressed by the following formula b:

formula b wherein Y represents a substituted or an unsubstituted phenyl group; and q represents an integer of 1 to 4. Y is preferably 3,4-methylenedioxyphenyl group and q is preferably 2.

Benzyl group found at $R_1$ can have a substituted group on its aromatic ring. For such benzyl group having a substituted group, piperonyl group can be cited, for example.

Carbamoyl group at $R_1$ can have a substituted group on its nitrogen atom. For such a substituted group, a lower alkyl group can be introduced. Here, the lower alkyl group can be exemplified by that of $R_2$ mentioned below. Preferably, it is a branched alkyl group and, particularly preferably, isopropyl group.

Pyridyl group at $R_1$ can have a substituted group on its pyridine ring and, preferably, unsubstituted pyridyl group.

In the present invention, the lower alkyl group found at $R_2$ is a straight or branched alkyl group having 1 to 6 carbon atoms. Examples thereof include methyl, ethyl, n-propyl, n-butyl, isopropyl, isobutyl, 1-methylpropyl, tert-butyl, n-pentyl, 1-ethylpropyl, isoamyl, and n-hexyl group. Preferably it is a branched lower alkyl group and, particularly preferably, isobutyl group.

The lower alkoxy group found at $R_2$ represents an alkoxy group derived from the above-mentioned lower alkyl group. A preferable example thereof is methoxy group.

An alkenyl group at $R_3$ refers to a straight or branched alkenyl group which has at least one double bond and has 2 to 20 carbon atoms. While the double bond has two kinds of configurations, namely, cis and trans, each double bond in alkenyl group may have either configurations. Among such a alkenyl group, a branched alkenyl group is preferable. Further, prenyl, geranyl, neryl or farnesyl group is preferable. Furthermore, prenyl or geranyl group is preferable.

Benzyl group found at $R_3$ can have a substituted group on its aromatic ring. A preferable example of such a substituted group is a halogen atom including chlorine, bromine, iodine, and fluorine atom. The most preferable example thereof is fluorine atom. Also, the fluorine atom is bonded to para-position, preferably.

A preferable compound of the present invention may be a compound in which $R_3$ is an alkenyl group in the above-mentioned formula 1. Particularly preferably, it may be expressed by the following formula 2:

formula 2 wherein
Ra represents methyl group or prenyl group;
$R_1$ represents a pyridylcarbonyloxy lower alkyl group, a benzoylamino lower alkyl group, or benzyl group; and
$R_2$, m, and n are same as those in the above-mentioned formula 1.

In the compound in which $R_3$ is an alkenyl group in formula 1, it is preferable that n is 1 or 2 and $R_2$ is isobutyl or methoxy group.

Also, in the compound in which $R_3$ is an alkenyl group in formula 1, it is preferable that n is 0.

A preferable compound of the present invention may be a compound in which $R_3$ is benzyl group, $R_2$ is a lower alkyl group, and both of n and m are 1 in the above-mentioned formula 1. Particularly preferably, it may be expressed by the following formula 3:

formula 3 wherein
$R_1$ represents carbamoyl, benzyl, or pyridyl group;
$R_2$ represents a lower alkyl group;
Rb represents a halogen atom; and
l represents 0 or 1.

In the formula 3, it is preferable that l is 1 and Rb is fluorine atom bonded to para-position.

In the compound in which $R_3$ is benzyl group, $R_2$ is a lower alkyl group, and both of n and m are 1 in the above-mentioned formula 1, it is preferable that $R_2$ is isobutyl group.

A preferable compound of the present invention may be expressed by the following formula 4:

formula 4 wherein $R_1$ represents benzyl or diphenylmethyl group, and $R_2$ represents a lower alkyl group.

In formula 4, $R_2$ is isobutyl group, preferably.

In the following, while an example of the method for manufacturing the compound of the present invention will be explained, it should not be restricted thereto.

Figure 1:
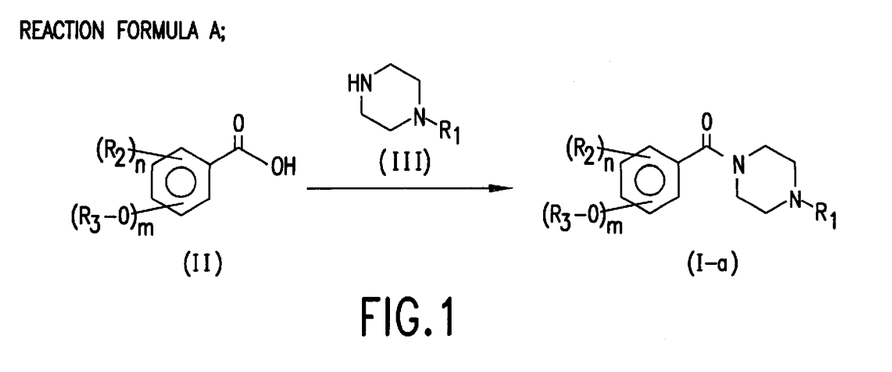
FIGS. 1 to 5 show examples of steps for manufacturing the N-acylpiperazine derivative in accordance with the present invention and FIGS. 6 to 9 show examples of steps for manufacturing material compounds for the N-acylpiperazine derivative in accordance with the present invention.

Among the compounds (I) of the present invention expressed by formula 1, the compound (I-a) in which $R_3$ is an alkenyl or benzyl group can be manufactured by reaction formula A shown in FIG. 1.

In reaction formula A, from a carboxylic acid (II) and a substituted piperazine (III), by using a known amide-bond forming reaction such as mixed anhydride method, acid chloride method, DCC method, or azide method, the N-acylpiperazine derivative (I-a) of the present invention can be obtained. Here, $R_1$ in the compound (III) and $R_2$, m, and n in the compound (II) are defined as formula 1 mentioned above, while $R_3$ in the compound (III) represents an alkenyl group or benzyl group.

In the mixed anhydride method, by using an activator such as diphenyl phosphinic chloride, ethyl chloroformate, isobutyl chloroformate, or pivaloyl chloride, the carboxylic acid (II) is converted into its corresponding anhydride and then reacted with the compound (III). As an additive, for example, an organic base such as triethyl amine, pyridine, or N-methylmorpholine can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as N,N-dimethylformamide or N,N-dimethylacetamide can be used. While the reaction temperature and reaction time may be changed according to the material compounds used, the reaction is usually effected at a temperature within the range of −15° C. to the reflux temperature of the solvent.

In the acid chloride method, as an activator, for example, phosphorus pentachloride, phosphorus trichloride, or thionyl chloride is used to convert the carboxylic acid (II) into the corresponding acid chloride and then the latter is reacted with the compound (III). As an additive, for example, an organic base such as triethyl amine, pyridine, or N-methylmorpholine can be used. As a solvent, for example, a halogenated hydrocarbon such as dichloromethane or chloroform; an aromatic hydrocarbon such as benzene, toluene, or xylene; or an amide such as N,N-dimethylformamide or N,N-dimethylacetamide can be used. While the reaction temperature and reaction time may be changed according to the material compounds used, the reaction is usually effected at a temperature within the range of 0° C. to the reflux temperature of the solvent.

In the DCC method, as a condensing agent, for example, N,N'-dicyclohexyl carbodiimide (DCC) or 1-ethyl-3-(3-dimethylaminopropyl)carbodiimide hydrochloride (WSCI) can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as N,N-dimethylformamide or N,N-dimethylacetamide can be used. If necessary, this reaction may be effected while 1-hydroxybenzotriazole (HOBt) or N-hydroxy succinimide (HOSu) is added thereto. While the reaction temperature and reaction time may be changed according to the material compounds used, the reaction is usually effected at a temperature within the range of 0° C. to the reflux temperature of the solvent.

In the azide method, as an activator, for example, diphenylphosphorylazide is used to convert the carboxylic acid (II) into the corresponding azide and then the latter is reacted with the compound (III). As an additive, for example, an organic base such as triethylamine, pyridine, or N-methylmorpholine can be used. As a solvent, for example, a halogenated hydrocarbon such as dichloromethane or chloroform; an aromatic hydrocarbon such as benzene, toluene, or xylene; or an amide such as N,N-dimethylfomamide or N,N-dimethylacetamide can be used. While the reaction temperature and reaction time may be changed according to the material compounds used, the reaction is usually effected at a temperature within the range of 0° C. to the reflux temperature of the solvent.

Specifically, for example, diphenylphosphinic chloride or pivaloyl chloride is used as an activator for the mixed anhydride method, while triethylamine is used as an additive to effect the reaction in a solvent such as chloroform or N,N-dimethyl formamide at a temperature within the range of −15° C. to room temperature, thereby attaining the aimed object.

Figure 2:
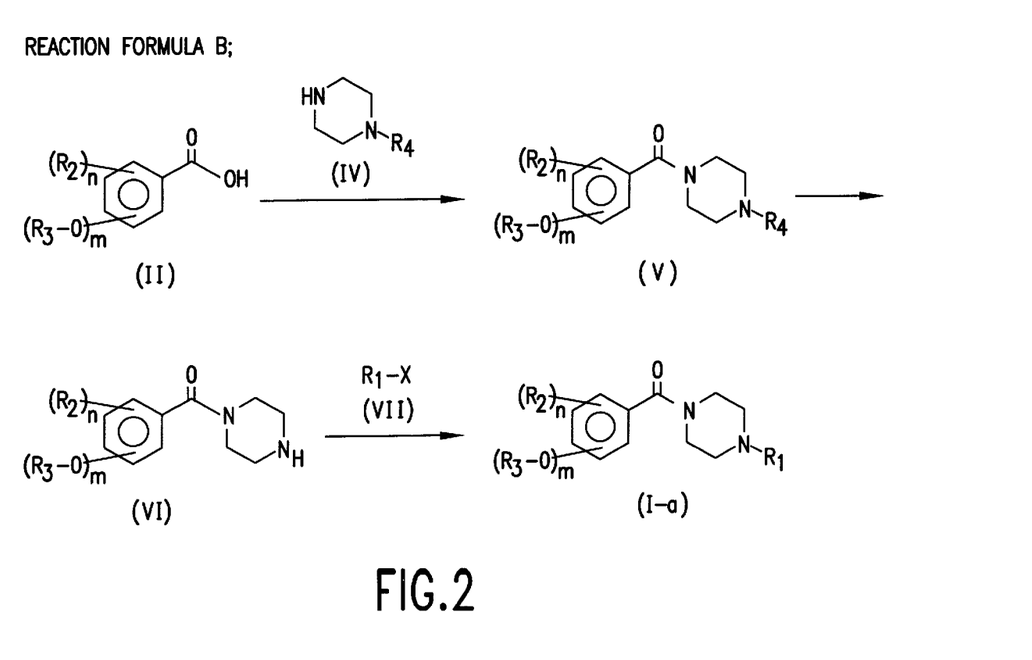

Also, the compound (I-a) in which $R_3$ is an alkenyl or benzyl group in formula 1 can be synthesized by reaction formula B shown in FIG. 2.

At the first step of reaction formula B, from a carboxylic acid (II) and a protected piperazine (IV), by using the condensation methods described in reaction formula A, a compound (V) can be obtained. In the compound (II), $R_2$, m, and n are defined as formula 1 mentioned above, while $R_3$ is an alkenyl or benzyl group. $R_4$ in the compound (IV) represents an amino-protecting group which can be a urethane type protecting group such as benzyloxycarbonyl group or tert-butyloxycarbonyl group, an acyl type protecting group such as formyl group or tosyl group, or an alkyl type protecting group such as trityl group as long as no problem occurs in the subsequent reaction.

At the second step of reaction formula B, the compound (V) is subjected to a deprotecting reaction so as to obtain a compound (VI).

For this deprotecting reaction, various kinds of known methods can be used according to the kind of the amino-protecting group $R_4$. For example, hydrazine, hydrochloric acid, hydrogen peroxide, or the like can be used as the deprotecting agent when $R_4$ is formyl group. Specifically, for example, hydrochloric acid within the range of 1N to 6N is used to effect the reaction in methanol at a temperature within 0° C. to room temperature, thereby attaining the aimed object.

At the third step of reaction formula B, the compound (VI) is reacted with a halogenated compound (VII) in the presence of a base so as to obtain the N-acylpiperazine derivative (I-a) of the present invention. In the compound (VII), X represents a halogen atom, while $R_1$ is defined as formula 1 mentioned above.

As a base, for example, an inorganic base such as potassium carbonate, potassium hydroxide, sodium hydroxide, or sodium hydride; or an organic base such as triethylamine or pyridine can be used. Specifically, for example, potassium carbonate is used as a base, and the reaction is effected in a solvent such as acetone, N,N-dimethylformamide, dichloromethane, or benzene at a temperature within the range of 0° C. to the reflux temperature of the solvent, thereby attaining the aimed object.

Figure 3:
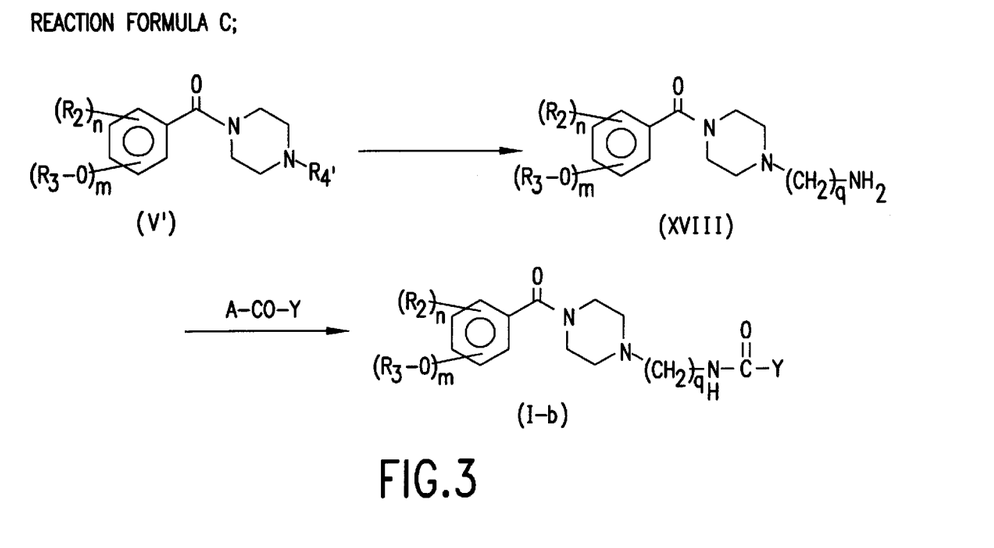

Among the compounds (I) of the present invention, a compound in which $R_1$ is a benzoylamino lower alkyl group, for example, a compound (I-b) can be synthesized by reaction formula C shown in FIG. 3.

At the first step of the reaction formula C, the compound (V), which can be synthesized by the first step of reaction formula B mentioned above, is subjected to a reduction so as to obtain an amine (XVIII). Here, $R_4'$ represents a cyanoalkyl group.

In reduction of the cyano group at this reaction, a known method can be used. For example, Birch reduction method, a reduction method by metal hydride complex compound, a method using Raney nickel, or the like can be used. In Birch reduction, while sodium or lithium is used mainly as a catalyst, the reaction can be effected in the mixed solvent of liquid ammonia and alcohol such as methanol or ethanol. When the metal hydride complex compound is used, as a reagent, lithium aluminum hydride, aluminum hydride, sodium borohydride, or the like can be used. As a solvent, for example, an ether such as diethylether, tetrahydrofuran or dioxane; or an alcohol such as methanol, ethanol, or butanol can be used. When sodium borohydride is used, Raney nickel, aluminium chloride, cobalt chloride, or the like can be used as a catalyst. When Raney nickel is used, methanol saturated by ammonia is used as a solvent and hydrogenation is effected under a pressure, thereby attaining the aimed object. While the reaction temperature and reaction time may be changed according to the material compounds used in all cases, the reaction is usually effected at a temperature within the range of 0° C. to the reflux temperature of the solvent.

Specifically, for example, lithium aluminum hydride is suspended in tetrahydrofuran while being cooled with ice and, after the compound (XIII) is dropped thereto, the reaction is effected at a temperature within the range of 0° C. to the reflux temperature of the solvent. Then, the reaction solution is treated with water, aqueous sodium hydroxide solution, or the like, thereby attaining the aimed object.

At the second step of the reaction formula C, by amidation of the compound (XVII) with A—CO—Y, the compound (I-b) of the present invention can be obtained Here, Y is defined as that of formula b mentioned above, while A represents hydroxy group, a halogen atom, or —OCOY. This amidation can be effected under a reaction condition similar to that of reaction formula A.

Figure 4:
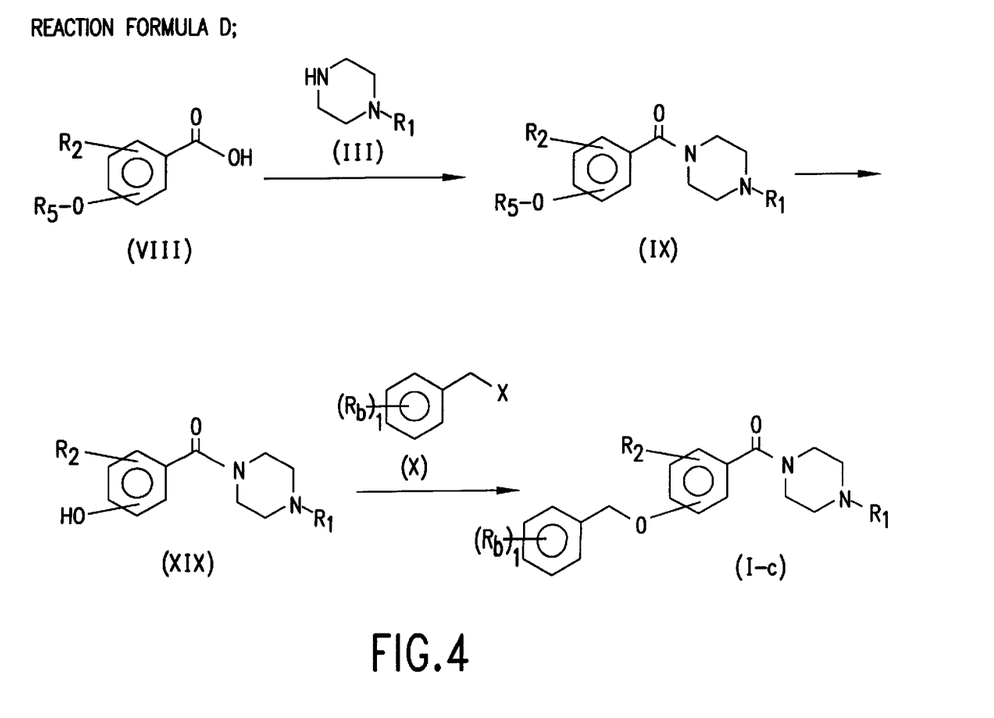

Among the compound (I) of the present invention, a compound in which $R_3$ is benzyl group, for example, a compound expressed by the above-mentioned formula 3 can be synthesized by reaction formula D shown in FIG. 4.

At the first step of reaction formula D, from a carboxylic acid (VIII) and the substituted piperazine (III), by using the condensation method described in reaction formula A, a compound (IX) can be obtained. $R_1$ in the compound (III) and $R_2$ in the compound (VIII) are defined as those of formula 1. $R_5$ in the compound (VIII) represents a protecting group for a phenolic hydroxy group. As long as no problem occurs in the subsequent reaction, benzyl group, various kinds of substituted benzyl groups, benzyloxycarbonyl group, tert-butyloxycarbonyl group, and the like can be used therefor.

At the second step of reaction formula D, the compound (IX) is subjected to a deprotecting reaction so as to obtain the compound (XIX) in which $R_5$ is hydrogen atom.

For this deprotecting reaction, various kinds of known methods can be used according to the kind of the protecting group $R_5$. For example, when $R_5$ is benzyl group, reductive elimination method or acid-treated elimination method can be used. Specifically, for example, under a catalytic reduction condition, by using palladium-carbon as a catalyst, a reaction is effected in a solvent such as ethanol under a hydrogen gas atmosphere at a temperature within the range of room temperature to the reflux temperature of the solvent, thereby attaining the aimed object.

At the third step of reaction formula D, the compound (XIX) is reacted with the appropriately substituted benzyl halide (X) in the presence of a base so as to obtain the compound (I-c) of the present invention in which $R_3$ is benzyl group. In the compound (X), Rb and l are defined as those of formula 3, while X represents a halogen atom.

As a base in this reaction, for example, an inorganic base such as potassium carbonate, potassium hydroxide, sodium hydroxide, and sodium hydride; or an organic base such as triethylamine and pyridine can be used. Specifically, for example, potassium carbonate is used as a base so as to effect a reaction in a solvent such as acetone and N,N-dimethylformamide at a temperature within the range of room temperature to the reflux temperature of the solvent, thereby attaining the aimed object.

Here, as in the case of reaction formula D, a compound in which $R_3$ is hydrogen atom or benzyl group and neither of n nor m is 1 in the compound (I) of the present invention can be synthesized.

Figure 5:
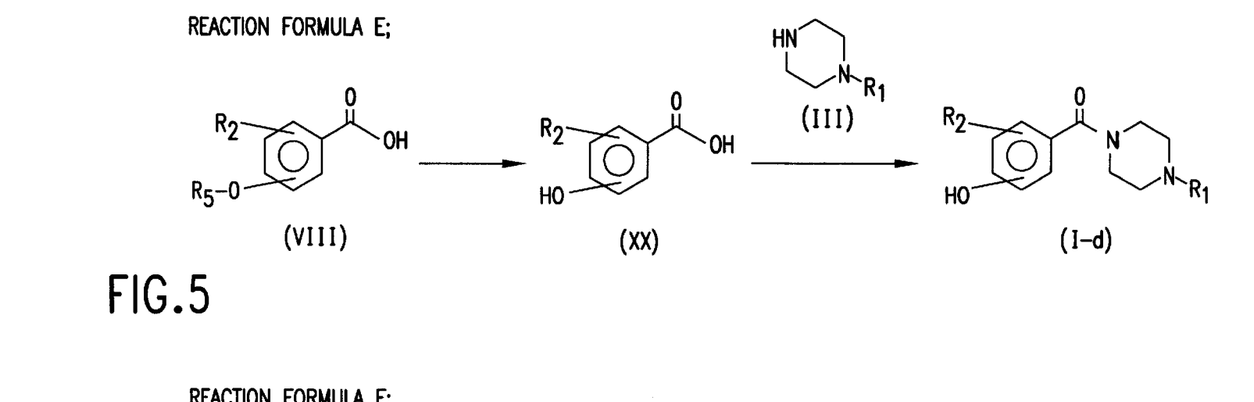

Among the compound (I) of the present invention, the compound in which $R_3$ is hydrogen atom and $R_1$ is benzyl group or diphenylmethyl group, for example, a compound expressed by formula 4 mentioned above can be synthesized by reaction formula E shown in FIG. 5.

At the first step of reaction formula E, the compound (VIII) is subjected to a deprotecting reaction so as to obtain a compound (XX). This reaction can be effected under the condition similar to that of the second step of reaction formula D.

At the second step of reaction formula E, from the carboxylic acid (XX) and the substituted piperazine (III), by using the condensation method described in reaction formula A, a compound (I-d) of the present invention can be obtained. $R_1$ in the compound (III) and $R_2$ in the compound (VIII) are defined as those of formula 4.

In the following, a manufacturing method of each material compound will be explained.

The material compound (II) in reaction formula A and B may be commercially available or can be synthesized by a known method. For example, the material compound (II-a) in which $R_3$ is benzyl group and both of n and m are 1 in the material compound (II) can be manufactured by reaction formula F shown in FIG. 6.

Figure 6:
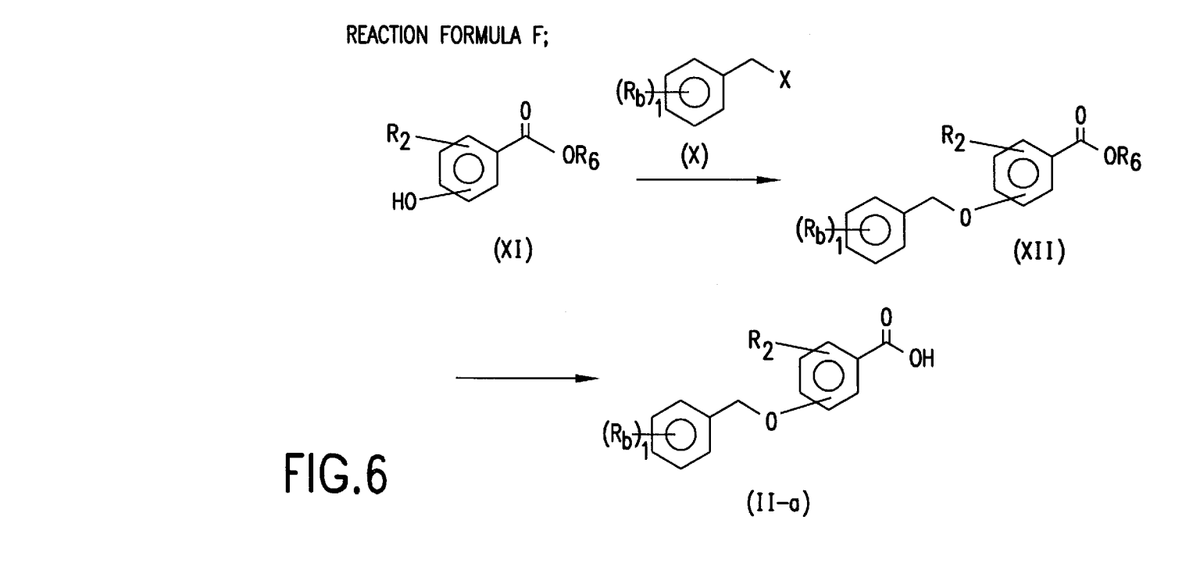

At the first step of reaction formula F, the compound (XI) is reacted with the substituted benzyl halide (X) in the presence of a base to obtain the compound (XII). $R_2$ in the compound (XI) is defined as that of formula 1, while Rb and l in the compound are defined as those of formula 3. X in the compound (X) represents a halogen atom. $R_6$ in the compound (XI) represents a carboxyl-protecting group which may be a lower alkyl group such as methyl group, ethyl group, or tert-butyl group, phenacyl group, or trichloroethyl group as long as no problem occurs in the subsequent reaction.

As a base in this reaction, for example, an inorganic base such as potassium carbonate, potassium hydroxide, sodium hydroxide, and sodium hydride; or an organic base such as triethylamine and pyridine can be used. Specifically, for example, potassium carbonate is used as a base so as to effect a reaction in a solvent such as acetone and N,N-dimethylformamide at a temperature within the range of room temperature to the reflux temperature of the solvent, thereby attaining the aimed object.

At the second step of reaction formula F, the compound (XII) is subjected to a deprotecting reaction so as to obtain the carboxylic acid (II-a).

For this deprotecting reaction, various kinds of known methods can be used according to the kind of the protecting group $R_6$. For example, when $R_6$ is methyl or ethyl group, known ester hydrolysis method can be used for deprotection. Specifically, for example, an inorganic base such as sodium hydroxide and potassium hydroxide is used so as to effect a reaction in a solvent such as water, methanol, and ethanol at a temperature within the range of room temperature to the reflux temperature of the solvent, thereby attaining the aimed object.

Figure 7:
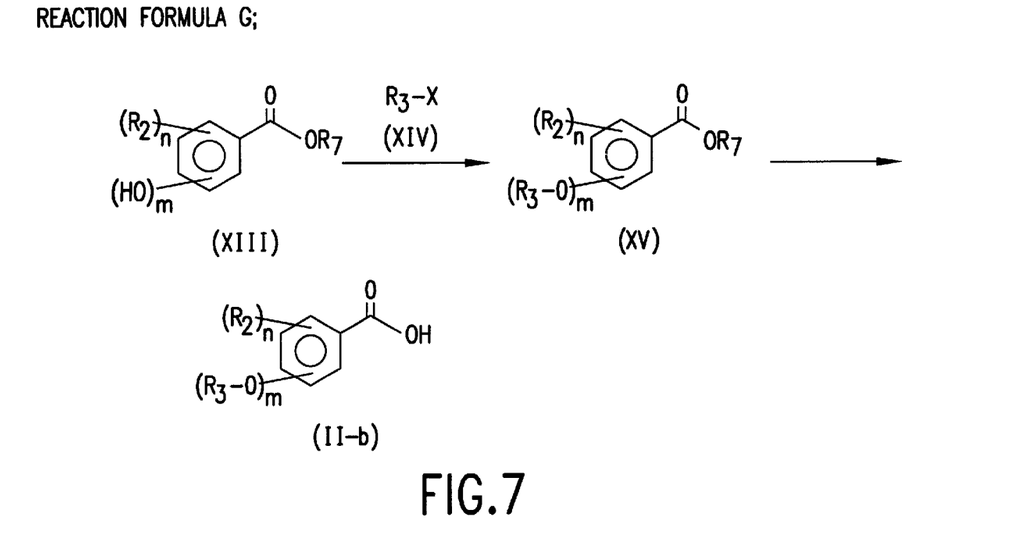

Among the material compound (II) in reaction formula A and B, for example, a compound (II-b) in which $R_3$ is an alkenyl group can be synthesized by reaction formula G shown in FIG. 7.

In reaction formula G, $R_2$, m, and n in the compound (XIII) are defined as those of formula 1. $R_7$ represents a carboxyl-protecting group which may be a lower alkyl group such as methyl group, ethyl group, and tert-butyl group; phenacyl group; or trichloroethyl group as long as no problem occurs in the subsequent reaction. $R_3$ in the compound (XIV) represents an alkenyl group, while X represents a halogen atom.

In reaction formula G, an alkenyl halide (XIV) is reacted with a compound (XIII) in the presence of a base and then hydrolyzed so as to synthesize the carboxylic acid (II-b).

The first step of this reaction can be effected in the presence of a base. Sodium amide, triethylamine, sodium hydride, sodium hydroxide, potassium carbonate, barium oxide, silver oxide, or the like can be used therefor. Also, a catalytic amount of potassium iodide can be added thereto. As a solvent, for example, an alcohol such as methanol, ethanol, and butanol; an aromatic compound such as benzene, toluene, xylene, and pyridine; an ether such as diethylether, tetrahydrofuran, and dioxane; an amide such as N,N-dimethylformamide and N,N-dimethylacetamide; or a ketone such as dimethylsulfoxide and acetone can be used. While the reaction temperature and reaction time may be changed according to the material compounds used, the reaction is usually effected at a temperature within the range of 0° C. to the reflux temperature of the solvent.

Specifically, for example, the compound (XIII) is dissolved in tetrahydrofuran or N,N-dimethylformamide and, after sodium hydride as a base is added and stirred therein, the alkenyl halide is added thereto so as to effect a reaction at a temperature within the range of room temperature to the reflux temperature of the solvent, thereby attaining the aimed object.

In the reaction of the second step, the ester compound (XV) is hydrolyzed in the presence of an acid or a base so as to synthesize the carboxylic acid (II-b). Hydrochloric acid, sulfuric acid, p-toluenesulfonic acid, or the like can be used as the acid, while sodium hydroxide, potassium hydroxide, potassium t-butoxide, or the like can be used as a base. As a solvent, a carboxylic acid such as formic acid and acetic acid; an alcohol such as methanol and ethanol; water; or a mixed solvent thereof can be used. While the reaction temperature and reaction time can be changed according to the material compounds used, the reaction is usually effected at a temperature within the range of 0° C. to the reflux temperature of the solvent.

Specifically, for example, the ester compound (XV) is dissolved in an alcohol such as methanol and ethanol and then an aqueous sodium hydroxide or potassium hydroxide solution is added thereto so as to effect a reaction at a temperature within the range of room temperature to the reflux temperature of the solvent, thereby attaining the aimed object.

Figure 8:
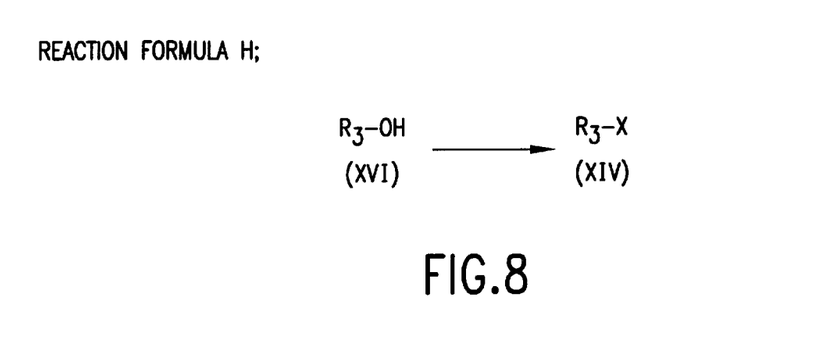

The material compound (XIV) used in reaction formula G can be synthesized by reaction formula H in FIG. 8.

In reaction formula H, X and $R_3$ are defined as those of reaction formula G. In this reaction, by halogenation of an alcohol (XVI), an alkenyl halide (XIV) can be obtained.

For this reaction, a general method known as halogenation of hydroxy group can be used. As a reagent of halogenation, for example, a strong acid such as hydrochloric acid or hydrobromic acid; a phosphorus compound such as phosphorus tribromide, phosphorus trichloride, or phosphorus pentachloride; thionyl chloride; N-halogenosuccinimide and methyl sulfide; triphenylphosphine and a halogenated hydrocarbon; or methanesulfonyl chloride and lithium halide is used to effect the reaction. As a solvent, for example, a halogenated hydrocarbon such as dichloromethane and chloroform; an aromatic compound such as benzene, toluene, xylene, and pyridine; an ether such as diethylether, tetrahydrofuran and dioxane; or an amide such as N,N-dimethylformamide or N,N-dimethylacetamide can be used. While the reaction temperature and reaction time may be changed according to the material compounds used, the reaction is usually effected at a temperature within the range of 0° C. to the reflux temperature of the solvent.

Specifically, for example, in the presence of lithium chloride and triethylamine, methanesulfonyl chloride is used so as to effect a reaction in a solvent such as acetone at a temperature within the range of 0° C. to room temperature, thereby attaining the aimed object.

Figure 9:
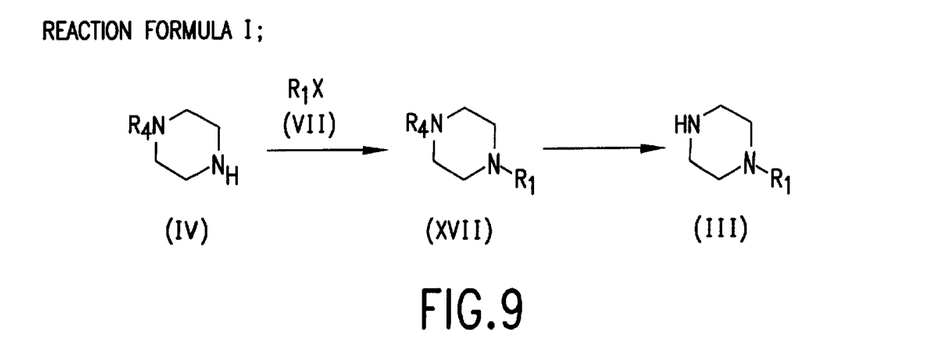

The material compound (III) in reaction formula A and D may be commercially available or can be synthesized by reaction formula I in FIG. 9.

At the first step of reaction formula I, the protected piperazine (IV) is reacted with the appropriate halide (VII) in the presence of a base so as to obtain the compound (XVII). $R_4$ in the compound (IV) represents an amino-protecting group which can be a urethane type protecting group such as benzyloxycarbonyl group and tert-butyloxycarbonyl group; an acyl type protecting group such as formyl group and tosyl group; or an alkyl type protecting group such as trityl group as long as no problem occurs in the subsequent reaction. X in the compound (VII) represents a halogen atom.

As a base, for example, an inorganic base such as potassium carbonate, potassium hydroxide, sodium hydroxide, and sodium hydride; or an organic base such as triethylamine and pyridine can be used. Specifically, for example, potassium carbonate is used as a base so as to effect a reaction in a solvent such as acetone, N,N-dimethylformamide, dichloromethane, and benzene at a temperature within the range of 0° C. to the reflux temperature of the solvent, thereby attaining the aimed object.

At the second step of reaction formula I, the compound (XVII) is subjected to a deprotecting reaction so as to obtain the compound (III).

For this deprotecting reaction, various kinds of known methods can be used according to the kind of the amino-protecting group $R_4$. For example, hydrazine, hydrochloric acid, hydrogen peroxide, or the like can be used as the deprotecting agent when $R_4$ is formyl group. Specifically, for example, hydrochloric acid within the range of 1N to 6N is used to effect the reaction in methanol at a temperature within the range 0° C. to room temperature, thereby attaining the aimed object.

Among the material compounds used in the above-mentioned reaction formulas, those with no preparation methods described, for example, compound (IV), (VII), (VIII), and (X), may be commercially available or easily synthesized by using a known method.

Also, examples of salts of the N-acylpiperazine derivative (I) of the present invention with an acid include salts with inorganic acids such as hydrochloric acid, hydrobromic acid, sulfuric acid, and phosphoric acid and salts with organic acids such as acetic acid, propionic acid, citric acid, lactic acid, oxalic acid, maleic acid, fumaric acid, succinic acid, tartaric acid, and methane sulfonic acid. These salts can be easily manufactured by a normal method.

The N-acylpiperazine derivative in accordance with the present invention has a strong effect against stress ulcer and an excellent effect for suppressing gastric acid secretion. Further, it has an antibacterial activity against *Helicobacter pyroli* which is supposed to be a cause for recurrence of ulcer. Furthermore, it has a high safety. Accordingly, it is useful as a medicament for curing and preventing peptic ulcer in man or mammals and, particularly, gastric ulcer in man. Conventionally, there has hardly been known such a compound which has both effect for suppressing gastric acid secretion and antibacterial activity against *Helicobacter pyroli*. Accordingly, it is indicated that the compound of the present invention is not only effective in preventing and curing ulcer but also in preventing the recurrence thereof.

When the compound of the present invention is administered as a medicament for curing and preventing peptic ulcer, it may be administered orally as tablet, powder, granule, capsule, syrup, or the like as well as parenterally as suppository, injection, external drug, instillation or the like. While the amount of administration may be outside of the range mentioned below according to the degree of symptom, personal difference, age, kind of ulcer, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide. Examples of the binder include polyvinylalcohol, polyvinylether, ethyl cellulose, methyl cellulose, gum arabic, tragacanth, gelatin, shellac, hydroxypropyl cellulose, hydroxypropyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When preparing an injection, if necessary, a pH-adjusting agent, a buffer, a stabilizer, a solubilizer, and the like are added to the main medicament and then a normal method is used to form subcutaneous, intramuscular, and intravenous injection drugs.

In the following, the present invention will be explained in further detail by specifically examples. However, the present invention should not be restricted to these examples.

First, test methods used for evaluating these examples will be explained.

WIS: Restraint and Water Immersion Stress-Induced Ulcer Inhibition Test i) Meaning The degree of inhibition of the stress ulcer formation is tested.

ii) Method

Male Crj:SD or Slc:SD rats (6 to 7-week-old) were fasted overnight, but allowed free access to water. Each group has 5 to 8 of these rats. The sample compound was dissolved or suspended in an aqueous solution of 0.3% sodium carboxymethylcellulose or 0.05% Tween 80 and then was orally administered (100 mg/10 ml/kg). To a control group, the vehicle was administered. 10 minutes later, the rats were placed in a stress cage and immersed to the level of xipfoid process in a water bath (21° C.) for 7 hours. At the end of the stress, the rats were sacrificed by inhalation of ether or carbon dioxide. Then, the stomach of each was removed, inflated by injecting 10 ml of 5% formalin neutral buffer solution, and immersed in 1% formalin neutral buffer solution for 30 minutes or more to be fixed. The stomach was incised along the greater curvature and then the length of each erosion in the glandular portion was determined under dissecting microscope. The sum of the length of erosions per stomach was defined as ulcer index (UI).

iii) Judgment Standard

The effect obtained when 100 mg/kg of the sample compound had been administered was expressed as ulcer formation inhibitory rate (%) as follows:

ulcer formation inhibitory rate (%)=(1−(UI in sample group/UI in control group))×100

CAP: Acid Secretion Inhibition Test In Vitro i) Meaning

The acid secretion inhibitory activity in a cell level is studied. It can also be used for studying the mechanism of the effect.

ii) Method ii-a) Preparation of Isolated Gastric Fundus Gland Suspension

First, an isolated gastric fundic gland sample was prepared. Namely, a male Japanese White rabbit (2.5 to 3 kg) was anesthetized to death with Nembutal™ and then the abdomen was incised. Immediately thereafter, the stomach was removed and, after its pyloric and cardiac antrum were severed, incised along its greater curvature into two sheets. The gastric contents adhering to the mucosal surface was washed out with ice-cooled PBS (−) and then carefully washed therein. The gastric wall was spread on a cork board with its mucosal surface facing up and the feed and mucus thereon were completely removed with sterile gauze. The mucosa was separated therefrom by a spatula and then collected in ice-cooled PBS (−). After being washed twice with PBS (−), the mucosa was minced into 2–3 mm$^3$ pieces by scissors. These pieces were further washed twice with a nutrient solution. The nutrient solution comprises 132.4 mM of NaCl, 5.4 mM of KCl, 5 mM of $Na_2HPO_4.12H_2O$, 1 mM of $NaH_2PO_4.2H_2O$, 1.2 mM of $MgSO_4$, 1 mM of $CaCl_2$, 25 mM of HEPES, 2 mg/ml of glucose, and 1 mg/ml of BSA. Into 70 ml of the nutrient solution containing 1 mg/ml of collagenase, minced mucosal pieces were dispersed and intensely stirred in a conical flask with a stirrer at 37° C. for 40 to 60 minutes. During this period, 100% $O_2$ was sprayed on the nutrient solution surface and the pH was appropriately measured such that it was immediately adjusted to pH 7.4, when the value was therebelow, with a base. The nutrient solution was added to the reaction solution so as to attain the total amount of about 200 ml. After being filtered through a mesh, the suspension was divisionally introduced into 50 ml centrifuge tubes and left for 15 minutes such that gastric fundic gland was deposited. The supernatant was repeatedly removed by an aspirator, dispersed in the nutrient solution, and then left such that the gastric fundic gland was washed three times. At this time, without using a pipette, the suspension was alternately introduced into two centrifuge tubes so as to effect dispersion. The number of cells was counted under microscope and adjusted to $1.6 \times 10^6$ cells/ml.

ii-b) [$^{14}$C]-aminopyrine Uptake Test

Then, [$^{14}$C]-aminopyrine uptake test was performed. After an Eppendorf tube was weighed, 10 µl (final concentration: $10^{-5}$M) of histamine dissolved in the above-mentioned nutrient solution, 10 µl (final concentration: $10^{-5}$M) of the test compound dissolved in DMSO, and 10 µl (final concentration: 0.05 µCi/ml) of [$^{14}$C]-aminopyrine diluted with the nutrient solution were introduced therein and then 970 µl of the isolated gastric fundic gland suspension prepared above was added thereto. Subsequently, this mixture was shaken at 37° C. for 40 minutes at 125 cycles/minute. After being centrifuged for 30 minutes, 200 µl of its supernatant was collected into a mini-vial, while the rest was removed by an aspirator. The gland pellet was completely dried as the tube with its lid being opened was kept for one night in a drying oven at 80° C. and then the lid was closed and the weight was determined at room temperature. Then 100 µl of 1N KOH was added thereto and the tube with its lid being closed was treated at 60° C. for 1 to 2 hours so as to dissolve the pellet. Then, the contents thereof were transferred to a mini-vial. Into the mini-vial containing the supernatant or gland pellet, 4 ml of Atomlite™ was added and then the radioactivity was measured by a liquid scintillation counter. Here, after the radioactivity of the gland pellet was corrected by using a sample in which 20 mM of NaSCN was added so as to cancel the hydrogen ion concentration gradient, the integration ratio of aminopyrine specifically trapped by the gland pellet was calculated. This experiment was performed in duplicate.

ii-c) Calculation of the Accumulation Rate of Aminopyrine

Here, its principle will be briefly explained. In the isolated gastric fundic gland, acid is accumulated in a space between its secretory tubule and intraglandular cavity. Aminopyrine is weak base (pKa=5.0) and nonionic in a neutral solution so as to freely pass through the cell membrane, whereas it is ionized in an acidic solution and thus cannot pass through the cell membrane due to its electric charge. Therefore, aminopyrine is accumulated in a closed acidic space within the isolated gastric fundic gland. In view of this characteristic, the accumulation rate (R) of aminopyrine is calculated by the following equation:

R=((corrected radioactivity of precipitate)/(radioactivity of supernatant))×(200/(mg dry weight of gland pellet))

iii) Judgment Standard

The effect of the sample compound at the final concentration of $10^{-5}$M was expressed by acid secretion inhibitory rate (%) as follows:

acid secretion inhibitory rate (%)=(1–(R in sample group/R in control group))×100

AHP: Antibacterial Activity Test Against *Helicobacter pyroli* i) Meaning

The minimum inhibitory concentration (MIC) against *Helicobacter pyroli* (microaerophilic gram-negative bacterium which is supposed to deeply involve in pathogenesis, relapse, and recrudescence of ulcer, referred to as "HP" in the following) is measured so as to find out compounds which have antimicrobial activity against *Helicobacter pyroli*.

ii) Method

MICs were determined by the agar dilution method. The stock culture (–80° C.) of HP NCTC 11637 was thawed and cultured on tripticase soy agar supplemented with 5% sheep blood at 37° C. in an atmosphere of 5% $O_2$, 10% $CO_2$, and 85% $N_2$. Grown colonies were transferred to the same plate and precultured for 3 days under the same condition.

A 1,000 µg/ml solution of the sample compound containing DMSO not more than 25% was seriesly diluted to be various concentrations 2-fold in sterile purified water. 100 µl volume from each dilution was mixed thoroughly with 900 µl of brucella agar supplemented with 5% horse blood and solidified in a 24 well micro plate, thereby yielding an MIC measurement plate.

An appropriate amount of the colony grown on the plate by preculturing was suspended in Mueller Hinton broth till turbidness was recognizable by naked eyes (a bacterial suspension containing about $10^7$ cfu/ml of the bacteria), and diluted 100-fold in the same broth; this resulted in a bacterial suspension for inoculation containing about $10^5$ cfu/ml of the bacteria.

10 µl of the bacterial suspension for inoculation (about $10^3$ cfu) was inoculated on this plate and cultured for 7 days under the same condition as that of preculture. Thereafter, it was judged whether there had been bacteria growth or not.

iii) Judgment Standard

The minimum concentration of the sample compound when there were no visible colonies or, if any, 5 or less colonies of HP was defined as MIC (µg/ml).

Here, when the MIC value was 100 µg/ml or more, in a manner similar to the above-mentioned method, both of a MIC measurement plate with a 250 mM solution of the sample compound and a MIC measurement plate for control without a sample compound were prepared and then the bacteria was inoculated thereon in a manner similar to the above-mentioned method. As the result of the comparison of these plates, when the number of the colony on the plate containing the sample compound was less than 90% with respect to that on the control plate, it was represented by "+". Contrary to this, when there was 90% or more, it was represented by "–".

AT: Single Dose Toxicity Pretest i) Method

Male Slc:ICR mice (5-week-old) were used. Each group has 3 to 5 mice and each mouse was fasted, but allowed free access to water, for 4 to 5 hours from 9 a.m. in the test day. Then, 2,000 mg/10 ml/kg of the sample compound dissolved or suspended in an aqueous solution of 0.5% sodium carboxymethyl cellulose was orally administered thereto. To a control, only the vehicle was administered. The behavior and symptom were observed at each of 15 minutes, 30 minutes, 1 hour, 2 hours, and 3 hours after the administration and then daily till one week thereafter. The body weight was measured before and after the fasting as well as at the same time everyday. The dead animals were immediately subjected to autopsy and their organs were observed microscopically. Also, the living animals were sacrificed with ether or carbon dioxide one week after the administration and then their organs were observed microscopically.

ii) Judgment Standard

The toxicity at the single dose of 2,000 mg/kg of the sample compound was expressed as being classified into 5 levels.

5: Mortality rate is 0%; no toxicity is found at all both in behavior and organs.

4: Mortality rate is 0%; while no toxicity is found in organs, slight toxicity is observed in behavior and body weight increase.

3: While there is a dead animal (though not all the animals are dead), no toxicity is found in organs.

2: Regardless of whether there is a dead animal or not, toxicity is found in organs.

1: All the animals are dead.

MTT: Cell Damaging and Protecting Effect Test i) Meaning

It is confirmed that there is no toxicity in cell level. Those having a toxicity in cell level are inappropriate as an anti-ulcer drug. Also, it can be confirmed that the effects of the sample compounds in other cell level tests do not result from their toxicity.

ii) Method

A male Japanese White rabbit (2.5 to 3 kg) was anesthetized to death by Nembutal™ and, immediately thereafter, its stomach was removed. The greater curvature of the stomach was incised so as to remove the stomach contents therefrom. After the mucosal surface was washed with HBSS (Hanks' Balanced Salt Solution), the stomach in ice-cooled HBSS was transferred to a laboratory. Then, after the pyloric antrum was removed, the gastric corpus mucosa was separated by a spatula and then minced into 2 to 3 mm$^3$ pieces in BME (Basal Medium Eagle). Thereafter, these pieces were shaken at 120 to 130 cycles/minute for 15 minutes at 37° C. in BME 60 ml containing 280 U/ml of dispase and 30 to 50 U/ml of collagenase. Here, the concentration of collagenase was appropriately changed for each lot in view of the state of cells. The pieces were washed twice with EBSS (Earle's Balanced Salt Solution) containing 1 mM of EDTA and then shaken in MEM (Minimum Essential Medium) containing 1 mM of EDTA at 37° C. for 5 minutes. Subsequently, they were shaken in the dispase and collagenase having the same concentrations as those mentioned above for 15 minutes so as to remove the supernatant and then further shaken at 37° C. for 50 to 60 minutes at 120 to 130 cycles/minute. Then, after being washed twice with HBSS, Ham F12 containing 2% of Ultrocer G™ was used to attain the concentration of 1×10$^6$ cells/ml. Thus formed suspension was dispensed in each well of a 96-well plate by 200 μl. The plate was incubated in the atmosphere composed of 5% $CO_2$ and 95% air at 37° C. for three days so as to attain a confluent state and then subjected to MTT assay.

The sample compound was dissolved in DMSO so as to attain a concentration of 10$^{-2}$M and then diluted with HBSS containing 2% of Ultrocer G™ so as to attain a final concentration of 10$^{-4}$M. To each group, which 8 wells were used for, 10 μl of MTT reagent was added immediately after 100 μl of the medium in each well was exchanged for same volume of the resulting solution of the sample compound. After being incubated in an atmosphere composed of 5% $CO_2$ and 95% air at 37° C. for 4 hours, thus formed solution was centrifuged and then its supernatant was discarded. Subsequently, 100 μl of 100% ethanol was added to the residue so as to dissolve MTT formazan. Then, the absorbance (OD: 570 to 630) was measured by a microplate reader. This method utilizes a phenomenon in which MTT is changed to MTT formazan only by mitochondria of living cells so as to change color.

iii) Judgment Standard

The cell damaging or cell protecting effect of the sample compound at the final concentration of 10$^{-4}$M was expressed as cell damaging rate (%) as follows:

cell damaging rate (%)=(1-(absorbance in sample group/absorbance in control group))×100

Accordingly, the smaller rate value is better in the cell damage.

Based on the foregoing effect tests and safety tests, anti-ulcer effect, anti-bacterial effect against *Helicobacter pyroli*, and safety of the example compounds of the present invention were studied.

COMPOUND GROUP 1

The N-acylpiperazine derivative in this compound group 1 is a compound in which $R_3$ is an alkenyl group in formula 1. As the N-acylpiperazine derivatives corresponding to this compound group 1, the following example compounds were tested.

Example 1:

Example 2:

Example 3:

Example 4:

Example 5:

Example 6:

TABLE 1

| Example | Anti-ulcer Tests | | Anti-HP Test | Safety |
|---|---|---|---|---|
| | WIS | CAP | AHP | MTT |
| 1 | 81 | 100.5 | 3.13 μg/ml> | 21 |
| 2 | | 99.4 | | 22 |
| 3 | | 101.1 | | −24 |
| 4 | 43 | | + | −29 |
| 5 | | 99.2 | + | −50 |
| 6 | | 99.5 | | −16 |
| 7 | | 99.6 | | −44 |

As clearly from TABLE 1, the compounds in this compound group 1 have high antibacterial activity against *Heli-*

Example 7:

cobacter pyroli as well as excellent anti-ulcer effect and acid secretion inhibition effect. Also, it is understood that these compounds have high safety.

COMPOUND GROUP 2

The N-acylpiperazine derivative in this compound group 2 is a compound in which $R_3$ is benzyl group, $R_2$ is a lower alkyl group, and both of n and m are 1 in formula 1. As the N-acylpiperazine derivatives corresponding to this compound group 2, the following example compounds were tested.

Example 8:

Example 9:

Example 10:

TABLE 2

| Example | Anti-ulcer Tests CAP | Anti-HP Test AHP | Safety MTT | AT |
|---------|---------------------|------------------|------------|-----|
| 8 | 36.9 | 3.13 μg/ml> | −93 | |
| 9 | 94.6 | + | −32 | |
| 10 | 96.0 | | −34 | 5 |

As clearly from TABLE 2, the N-acylpiperazine derivatives in this compound group 2 having benzyl group at $R_3$ and an alkyl group at the neighboring position have high anti-ulcer effect, acid secretion inhibition effect, and antibacterial activity against *Helicobacter pyroli*. Also, it is understood that these compounds have very high safety.

COMPOUND GROUP 3

The N-acylpiperazine derivative in this compound group 3 is a compound in which $R_3$ is hydrogen atom, $R_2$ is a lower alkyl group, and both of n and m are 1 in formula 1. As the N-acylpiperazine derivatives corresponding to this compound group 3, the following example compounds were tested.

Example 11:

Example 12:

TABLE 3

| Example | Anti-ulcer Tests CAP | Anti-HP Test AHP | Safety MTT |
|---------|---------------------|------------------|------------|
| 11 | 93.1 | 3.13 μg/ml> | 5 |
| 12 | 41.9 | + | −12 |

As clearly from TABLE 3, N-acylpiperazine derivatives in this compound group 3 have high anti-ulcer effect, acid secretion inhibition effect, and antibacterial activity against *Helicobacter pyroli*. Also, it is understood that these compounds have high safety.

In the following, the manufacturing method of the example compounds of the present invention will be shown.

Example 1

Synthesis of 1-(4-geranyloxy)benzoyl-4-[2-(piperonyloylamino)ethyl]piperazine In a manner similar to Example 8, 4-geranyloxybenzoic acid (5.49 g) was subjected to a condensation reaction with cyanomethylpiperazine (2.75 g), thereby yielding an amide (7.19 g). This amide (2.29 g) was dissolved in methanol and cobalt chloride (2.86 g) and sodium borohydride (2.27 g) were added thereto while being cooled with ice. After being stirred at room temperature for 20 minutes, the reaction mixture was concentrated. The residue was dissolved in chloroform and then filtrated. the filtrate was concentrated, thereby yielding an amine (1.12 g).

The amine (1.12 g) was dissolved in methylene chloride and triethylamine (0.45 g) was added thereto. While being cooled with ice, the mixture, with piperonyloyl chloride (0.41 g) added thereto, was stirred at 0° C. for 1 hour. The reaction mixture was washed with sodium hydrogencarbonate aqueous solution and brine successively, dried over sodium sulfate anhydride, and then filtrated. The filtrate was concentrated and the resulting residue was purified by silica gel column chromatography (chloroform:methanol=50:1), thereby yielding 0.27 g (23%) of the aimed compound as pale yellow oil.

$^1$H-NMR (CDCl$_3$) δ: 7.37(2H, d, J=8.8Hz), 7.31–7.24 (2H, m), 6.91(2H, d, J=8.8Hz), 6.84(1H, d, J=8.8Hz), 6.57 (1H, s), 6.03(2H, s), 5.48(1H, t, J=6.4Hz), 5.09(1H, t, J=6.8Hz), 4.56(2H, d, J=6.4Hz), 3.80–3.50(4H, bs), 3.53 (2H, q, J=5.4Hz), 2.62(2H, t, J=5.9Hz), 2.17–2.03(4H, m), 1.74(3H, s), 1.68(3H, s), 1.61(3H,s).

Example 2

Synthesis of 1-(4-geranyloxy-3-isobutyl)benzoyl-4-[2-(piperonyloylamino)ethyl]piperazine In a manner similar to Example 8, 4-geranyloxy-3-isobutylbenzoic acid (1.51 g) was subjected to a condensation reaction with N-hydroxyethylpiperazine (0.65 g), thereby yielding an amide (1.95 g, 94%). This amide (1.95 g) was reacted with piperonyloyl chloride (0.93 g), thereby yielding 1.92 g (68%) of the aimed compound as pale yellow oil.

$^1$H-NMR (CDCl$_3$) δ: 7.63(1H, d, J=8.3Hz), 7.45(1H, s), 7.25(1H, d, J=8.3Hz), 7.15(1H, s), 6.84(1H, d, J=8.8Hz), 6.82(1H, d, J=8.3Hz), 6.04(1H, s), 5.45(1H, t, J=6.8Hz), 5.10(1H, t, J=6.4Hz), 4.55(2H, d, J=5.8Hz), 4.42(2H, t, J=5.8Hz), 3.82–3.40(4H, bs), 2.79(2H, t, J=5.8Hz), 2.58(4H, s), 2.49(2H, d, J=6.8Hz), 2.18–2.04(4H, m), 1.91(1H, n, J=6.4), 1.72(3H, s), 1.68(3H,s), 1.61(3H, s), 0.88(6H, d, J=6.4Hz).

Example 3

Synthesis of 1-(4-geranyloxy)benzoyl-4-(2-isonicotinoyloxyethyl)piperazine

In a manner similar to Example 8, 4-geranyloxybenzoic acid (8.23 g) was subjected to a condensation reaction with N-hydroxyethylpiperazine (3.91 g), thereby yielding an amide (11.6 g). This amide (1.93 g) was reacted with isonicotinoyl chloride (0.89 g), thereby yielding 1.13 g (46%) of the aimed compound.

m.p. 52.5–55.0° C.

$^1$H-NMR (CDCl$_3$) δ: 8.79(2H, d, J=5.8Hz), 7.84(2H, d, J=5.4Hz), 7.36(2H, d, J=8.8Hz), 6.91(2H, d, J=8.8Hz), 5.47(1H, t, J=6.8Hz), 5.09(1H, t, J=6.8Hz), 4.56(2H, d, J=6.4Hz), 4.50(2H, t, J=5.4Hz), 3.85–3.40(4H, bs), 2.81(2H, t, J=5.4) 2,58(4H, s), 2.19–2.06(4H, m), 1.74(3H, s), 1.68 (3H, s), 1.61(3H, s).

Example 4

Synthesis of 1-(4-geranyloxy)benzoyl-4-piperonylpiperazine

In a manner similar to Example 8, 4-geranyloxybenzoic acid (1.01 g) was subjected to a condensation reaction with N-piperonylpiperazine (0.97 g), thereby yielding 1.85 g (96%) of the aimed compound.

Example 5

Synthesis of 1-benzyl-4-(3,5-dimethoxy-4-geranyloxy)benzoylpiperazine

In a manner similar to Example 8, 3,5-dimethoxy-4-geranyloxybenzoic acid was subjected to a condensation reaction with N-benzylpiperazine, thereby yielding the aimed compound.

Example 6

Synthesis of 1-benzyl-4-(3,4,5-triprenyloxy)benzoylpiperazine

In a manner similar to Example 8, 3,4,5-triprenyloxybenzoic acid (1.12 g) was subjected to a condensation reaction with N-benzylpiperazine (0.57 g), thereby yielding 1.14 g (72%) of the aimed compound.

$^1$H-NMR (CDCl$_3$) δ: 7.27–7.32(2H, s), 6.60(2H, s), 5.52–5.60(1H, m), 5.44–5.52 (2H, m), 4.54(4H, d, J=6.3Hz), 4.50(2H, d, J=6.3Hz), 3.50–3.77(4H, m), 3.53(2H, s), 2.41–2.55(4H, m), 1.71–1.76(18H, m).

Example 7

Synthesis of 1-benzyl-4-(3,4-dimethoxy-5-geranyloxy)benzoylpiperazine

In a manner similar to Example 8, 3,4-dimethoxy-5-geranyloxybenzoic acid (1.00 g) was subjected to a condensation reaction with N-benzylpiperazine (0.56 g), thereby yielding 1.29 g (87%) of the aimed compound.

$^1$H-NMR (CDCl$_3$) δ: 7.26–7.32(5H, m), 6.62(2H, s), 5.45–5.53(1H, m), 5.04–5.12 (1H, m), 4.58(2H, d, J=6.4Hz), 3.85(6H, s), 3.45–3.90(4H, m), 3.54(2H, s), 2.35–2.59(4H, m), 2.05–2.10(4H, m), 1.72(3H, s), 1.67(3H, s), 1.60(3H, s).

Example 8

Synthesis of 1-[4-(4-fluorobenzyloxy)-3-isobutyl]benzoyl-4-(N-isopropyl carbamoyl)piperazine

[4-(4-fluorobenzyloxy)-3-isobutyl]benzoic acid (1.51 g) was dissolved in a mixture of chloroform (25 ml) and triethylamine (1.39 ml), and then diphenylphosphinic chloride (0.96 ml) was added thereto while being cooled with ice. After being stirred for 40 minutes, the mixture, with 1-isopropylcarbamoylpyridine (0.89 g) added thereto, was stirred for 1.5 hours at room temperature. The reaction mixture was washed with 1N sodium hydroxide aqueous solution and brine successively, dried over sodium sulfate anhydride, and then filtrated. The filtrate was concentrated under a vacuum. The residue was recrystallized from n-hexane/ethyl acetate, thereby yielding 1.66 g (73%) of the aimed compound as white crystals.

mp 166.8–167.9° C.

$^1$H-NMR (CDCl$_3$) δ: 7.39(2H, dd, J=8.8, 5.4Hz), 7.28–7.22(1H, m), 7.18(1H,s), 7.09(1H, t, J=8.8Hz), 6.89 (1H, d, J=8.3Hz), 5.06(2H, s), 4.23(1H, d, J=7.3Hz), 3.98 (1H, d, J=6.8Hz), 3.75–3.50(4H, bs), 3.39(4H, t, J=5.4Hz), 2.53(2H, d, J=7.3Hz), 2.02–1.85(1H, m), 1.17(6H, d, J=6.8Hz), 0.89(6H, d, J=6.4Hz).

Example 9

Synthesis of 1-(4-benzyloxy-3-isobutyl)benzoyl-4-benzylpiperazine

In a manner similar to Example 8, 4-benzyloxy-3-isobutylbenzoic acid was subjected to a condensation reaction with N-benzylpiperazine, thereby yielding the aimed compound.

Example 10

Synthesis of 1-[4-(4-fluorobenzyloxy)-3-isobutyl] benzoyl-4-(2-pyridyl) piperazine In a manner similar to Example 8, [4-(4-fluorobenzyloxy)-3-isobutyl] benzoic acid was subjected to a condensation reaction with N-(2-pyridyl)piperazine, thereby yielding the aimed compound.

Example 11

Synthesis of 1-(2-hydroxy-3-isobutyl)benzoyl-4-piperonyloylpiperazine

In a manner similar to Example 8, 2-hydroxy-3-isobutylbenzoic acid (0.50 g) was subjected to a condensation reaction with N-piperonylpiperazine (0.62 g), thereby yielding 0.64 g (62.7%) of the aimed compound.

$^1$H-NMR (CDCl$_3$) δ: 9.76(1H, s), 7.14(1H, d, J=7.4Hz), 7.07(1H, d, J=7.8Hz), 6.85(1H, s), 6.71–6.77(3H, m), 5.95 (2H, s), 3.73(4H, brt, J=5.0Hz), 3.45(2H, s), 2.52(2H, d, J=7.2Hz), 2.48(4H, brt, J=5.0Hz), 1.92–2.04(1H, m), 0.92 (6H, d, J=6.6Hz).

Example 12

Synthesis of 1-diphenylmethyl-4-(3-hydroxy-4-isobutyl)benzoylpiperazine

In a manner similar to Example 8, 3-hydroxy-4-isobutylbenzoic acid was subjected to a condensation reaction with N-diphenylmethylpiperazine (0.62 g), thereby yielding the aimed compound.

What is claimed is:

1. An N-acylpiperazine compound or a pharmaceutically acceptable salt thereof expressed by the following formula 1:

formula 1 wherein

R$_1$ represents a pyridylcarbonyloxy lower alkyl group, an unsubstituted or a substituted benzyl group, wherein said substituted benzyl group is a piperonyl, an unsubstituted or a substituted carbamoyl group, wherein said substituted carbamoyl group is a lower alkyl carbamoyl group, a pyridyl group, a diphenylemthyl group, or a benzoylamino lower alkyl group having the formula of:

wherein Y represents an unsubstituted or a substituted phenyl group, wherein said substituted phenyl group is 3,4-methylenedioxyphenyl, and q represents an integer of 1 to 4;

R$_2$ represents a lower alkyl or lower alkoxy group;

n represents an integer of 0 to 2;

R$_3$ represents an alkenyl group, or an unsubstituted or a substituted benzyl group, wherein said substituted benzyl group has a halogen atom; and m represents an integer of 1 to 3.

2. An N-acylpiperazine compound or a pharmaceutically acceptable salt thereof according to claim 1, wherein R$_3$ is an alkenyl group.

3. An N-acylpiperazine compound or a pharmaceutically acceptable salt thereof according to claim 2, which is expressed by the following formula 2:

formula 2 wherein

Ra represents methyl group or prenyl group;

R$_1$ represents a pyridylcarbonyloxy lower alkyl group, an unsubstituted or a substituted benzyl group wherein said substituted benzyl group is a piperonyl, a benzoylamino lower alkyl group having the formula of:

wherein Y represents an unsubstituted or a substituted phenyl group, wherein said substituted phenyl group is 3,4 -methylenedioxyphenyl, and q represents an integer of 1 to 4;

R$_2$ represents a lower alkyl group or a lower alkoxy group;

n represents an integer of 0 to 2; and m represents an integer of 1 to 3.

4. An N-acylpiperazine compound or a pharmaceutically acceptable salt thereof according to claim 2, wherein n is 1 or 2 and R$_2$ is isobutyl or methoxy group.

5. An N-acylpiperazine compound or a pharmaceutically acceptable salt thereof according to claim 2, wherein n is 0.

6. An N-acylpiperazine compound or a pharmaceutically acceptable salt thereof according to claim 1, wherein $R_3$ is an unsubstituted or a substituted benzyl group, wherein said substituted benzyl group has a halogen atom, $R_2$ is a lower alkyl group, and both of n and m are 1.

7. An N-acylpiperazine compound or a pharmaceutically acceptable salt thereof, which is expressed by the following formula 3:

formula 3 wherein
$R_1$ represents an unsubstituted or a substituted carbamoyl group, wherein said substituted carbamoyl group is a lower alkyl carbamoyl group,
an unsubstituted or a substituted benzyl group, wherein said substituted benzyl group is a piperonyl, or a pyridyl group;
$R_2$ represents a lower alkyl group;
Rb represents a halogen atom; and
l represents 0 or 1.

8. An N-acylpiperazine compound or a pharmaceutically acceptable salt thereof according to claim 7, wherein l is 1 and Rb is fluorine atom bonded to para-position.

9. An N-acylpiperazine compound or a pharmaceutically acceptable salt thereof according to claim 6, wherein $R_2$ is isobutyl group.

10. The N-acylpiperazine derivative or a pharmaceutically acceptable salt thereof according to claim 1, wherein said substituted group of said carbamoyl group is an isopropyl group.

11. An antibacterial drug against *Helicobacter pyroli* or an anti-ulcer drug comprising, as an effective ingredient, an N-acylpiperazine compound or a pharmaceutically acceptable salt thereof according to claim 1, together with a pharmaceutically acceptable carrier and/or adjuvant.

12. A method for treating peptic ulcers in mammals, which comprises administering an effective amount of an N-acylpiperazine compound or a pharmaceutically acceptable salt thereof according to claim 1 to said mammals.

13. A method according to claim 12, wherein said peptic ulcers are gastric ulcers in man.

14. A method for inhibiting acid secretion in stomach of mammals, which comprises administering an effective amount of an N-acylpiperazine compound or a pharmaceutically acceptable salt thereof according to claim 1 to said mammals.

15. A method for inhibiting growth of *Helicobacter pyroli* in stomach of mammals, which comprises administering an effective amount of an N-acylpiperazine compound or a pharmaceutically acceptable salt thereof according to claim 1 to said mammals.

16. A method for preventing peptic ulcers in mammals, which comprises administering an effective amount of an N-acylpiperazine compound or a pharmaceutically acceptable salt thereof according to claim 1 to said mammals.

17. A method according to claim 16, wherein said peptic ulcers are gastric ulcers in man.

18. A method for treating peptic ulcers in mammals, which comprises administering to said mammals an effective amount of N-acylpiperazine compound or a pharmaceutically acceptable salt thereof having the following formula 4:

formula 4 wherein $R_1$ represents an unsubstituted or a substituted benzyl group, or diphenylmethyl group, and $R_2$ represents a lower alkyl group, wherein said substituted benzyl group is a piperonyl.

19. A method for treating peptic ulcers in mammals according to claim 18, wherein said peptic ulcers are gastric ulcers in man.

20. A method for inhibiting acid secretion in stomach of mammals, which comprises administering to said mammals an effective amount of N-acylpiperazine compound or a pharmaceutically acceptable salt thereof having the following formula 4:

formula 4 wherein $R_1$ represents an unsubstituted or a substituted benzyl group, or diphenylmethyl group, and $R_2$ represents a lower alkyl group, wherein said substituted benzyl group is a piperonyl.

21. A method for inhibiting the growth of *Helicobacter pyroli* in stomach of mammals, which comprises administering to said mammals an effective amount of N-acylpiperazine compound or a pharmaceutically acceptable salt thereof having the following formula 4:

formula 4 wherein $R_1$ represents an unsubstituted or a substituted benzyl group, or diphenylmethyl group, and $R_2$ represents a lower alkyl group, wherein said substituted benzyl group is a piperonyl.

22. A method of preventing peptic ulcers in mammals, which comprises administering to said mammals an effective amount of N-acylpiperazine compound or a pharmaceutically acceptable salt thereof having the following formula 4:

formula 4 wherein $R_1$ represents an unsubstituted or a substituted benzyl group, or diphenylmethyl group, and $R_2$ represents a lower alkyl group, wherein said substituted benzyl group is a piperonyl.

23. A method of preventing peptic ulcers according to 22, wherein said peptic ulcers are gastric ulcers in man.

* * * * *